United States Patent
Rump et al.

(10) Patent No.: US 11,207,027 B2
(45) Date of Patent: Dec. 28, 2021

(54) PASSIVE SENSOR FOR WIRELESS DETECTING OF THE ELECTRIC EXCITATION OF MUSCLE CELLS

(71) Applicant: BIOTRONIK SE & Co. KG, Berlin (DE)

(72) Inventors: Jens Rump, Berlin (DE); Christian Moss, Berlin (DE)

(73) Assignee: BIOTRONIK SE & Co. KG, Berlin (DE)

(*) Notice: Subject to any disclaimer, the term of this patent is extended or adjusted under 35 U.S.C. 154(b) by 0 days.

(21) Appl. No.: 17/271,268

(22) PCT Filed: Aug. 12, 2019

(86) PCT No.: PCT/EP2019/071521
§ 371 (c)(1),
(2) Date: Feb. 25, 2021

(87) PCT Pub. No.: WO2020/048735
PCT Pub. Date: Mar. 12, 2020

(65) Prior Publication Data
US 2021/0307696 A1  Oct. 7, 2021

(30) Foreign Application Priority Data
Sep. 4, 2018 (EP) .................... 18192360

(51) Int. Cl.
*A61B 5/395* (2021.01)
*A61B 5/00* (2006.01)
(52) U.S. Cl.
CPC .......... *A61B 5/6869* (2013.01); *A61B 5/0004* (2013.01); *A61B 5/395* (2021.01); *A61B 5/6882* (2013.01); *A61B 2560/04* (2013.01)

(58) Field of Classification Search
CPC ..... A61B 5/6869; A61B 5/395; A61B 5/0004; A61B 5/6882; A61B 2560/04; A61B 5/0245; A61B 5/296; A61B 5/277
See application file for complete search history.

(56) References Cited

U.S. PATENT DOCUMENTS

2007/0010750 A1*  1/2007  Ueno ............... A61B 5/25
                                                    600/509
2007/0032734 A1   2/2007  Najafi et al.
(Continued)

FOREIGN PATENT DOCUMENTS

DE  10258845 A1  1/2004
EP  1115329 B1  1/2006
WO  2015099845 A1  7/2015

OTHER PUBLICATIONS

T. Matsuo, K. Iinuma and M. Esashi, "A Barium-Titanate-Ceramics Capacitive-Type EEG Electrode," in IEEE Transactions on Biomedical Engineering, vol. BME-20, No. 4, pp. 299-300, Jul. 1973, doi: 10.1109/TBME.1973.324197. (Year: 1973).*

(Continued)

*Primary Examiner* — Eric J Messersmith
(74) *Attorney, Agent, or Firm* — Buchanan Ingersoll & Rooney PC (57) ABSTRACT

The invention relates to an implantable sensor for detecting an electrical excitation of muscle cells, in particular cardiac muscle cells, wherein it is provided that the sensor comprises a dielectric component and a contact point for contacting muscle cells, which is connected to the dielectric component, so that an electric field in the dielectric component, and correspondingly a capacitance of the dielectric component, change with an electrical excitation of the muscle cells. The invention furthermore relates to a system comprising a sensor and an implant.

15 Claims, 9 Drawing Sheets

(56) References Cited

U.S. PATENT DOCUMENTS

| | | | | |
|---|---|---|---|---|
| 2008/0183247 A1* | 7/2008 | Harding | ............... | A61N 1/3684 |
| | | | | 607/60 |
| 2009/0024042 A1* | 1/2009 | Nunez | ................. | A61B 5/0215 |
| | | | | 600/486 |
| 2012/0056631 A1* | 3/2012 | Feddes | .................... | A61B 5/25 |
| | | | | 324/686 |

OTHER PUBLICATIONS

J. Song, N. Pesonen, H. Seppä and V. Viikari, "On the use of the intermodulation communication towards zero power sensor nodes," 2013 European Microwave Conference, 2013, pp. 124-127, doi: 10.23919/EuMC.2013.6686606. (Year: 2013).*

International Search Report (PCT/ISA/210) and Written Opinion (PCT/ISA/237) dated Nov. 29, 2019, by the European Patent Office as the International Searching Authority for International Application No. PCT/EP2019/071521.

Rehrig, et al., "Dielectric and electromechanical properties of barium titanate single crystals grown by templated grain growth", IEEE Transactions on Ultrasonics, Ferroelectrics and Frequency Control, Jul. 2000, vol. 47, No. 4, pp. 895-902.

* cited by examiner

PASSIVE SENSOR FOR WIRELESS DETECTING OF THE ELECTRIC EXCITATION OF MUSCLE CELLS

CROSS-REFERENCE TO RELATED APPLICATIONS

This application is the United States national phase under 35 U.S.C. § 371 of PCT International Patent Application No. PCT/EP2019/071521, filed on Aug. 12, 2019, which claims the benefit of European Patent Application No. 18192360.8 filed on Sep. 4, 2018, the disclosures of which are hereby incorporated by reference herein in their entireties.

TECHNICAL FIELD

The present disclosure relates to an implantable sensor for detecting an electrical excitation of muscle cells, in particular cardiac muscle cells.

BACKGROUND

It is known to detect the electrical excitation of muscle cells by way of hard-wired electrodes.

As a result of the associated problems, such as an increased risk of infection or a cable break, efforts are already in progress to develop cable-free solutions instead. One challenge is the need that a sensor has to be placed in the atrium, usually in close proximity to the sinoatrial node, which monitors the cardiac activity, in some therapeutic forms, in particular when treating tachycardia, in addition to the active therapy.

The signal transmission from the sensor to the active implant is achieved in the process by a cable connection. An alternative concept is that the sensor has a dedicated power supply system and transmits the signals wirelessly to the implant.

A problem(s) with power being actively supplied by way of a battery is a greater form factor as well as a limited service life. The sensor is accordingly more complex with respect to the design thereof.

In addition, a galvanic connection is needed with hard-wired electrodes, which is susceptible to mechanical faults.

The present disclosure is directed toward overcoming one or more of the above-mentioned problems, though not necessarily limited to embodiments that do.

SUMMARY

Proceeding from this, it is an object of the present invention to provide a sensor that is improved with respect to the aforementioned problem(s).

At least this object is achieved by an implantable sensor having the features of claim 1. Further embodiments are provided in the dependent claims and will be described hereafter.

According to claim 1, an implantable sensor for detecting an electrical excitation of muscle cells, and in particular of cardiac muscle cells, is disclosed, wherein the sensor is characterized by comprising a dielectric component as well as a contact point for electrically contacting muscle cells of a patient, which is connected to the dielectric component in an electrically conducting manner, so that an electric field in the dielectric component, and correspondingly a capacitance of the dielectric component, changes with an electrical excitation of the muscle cells.

The present invention thus advantageously makes it possible to passively measure the stimulus transmission of cardiac muscle cells, in particular for further signal processing in an active implant, based on the change in the electric field or the capacitance of the dielectric component, and more particularly without an autonomous energy supply of the sensor.

According to one embodiment, the sensor is a passive sensor.

According to one embodiment, it is furthermore provided that the sensor is designed to wirelessly transmit the detection of an excitation of the muscle cells to a medical device, and in particular an implantable medical device.

According to one embodiment, it is furthermore provided that the sensor includes an antenna structure, which is connected to the dielectric component.

According to one embodiment, it is provided in this regard that the antenna structure is connected to the dielectric component so that the adaptation of the antenna structure changes when the electric field in the dielectric component and the capacitance of the dielectric component change with an electrical excitation of the muscle cells.

This can be measured by way of a broadband electromagnetic signal, which is transmitted from the implant to the sensor. In principle, in particular all frequencies that are approved for wireless communication can be used for this purpose, however the range decreases with increasing frequency. In contrast, the sensitivity increases with the frequency. Accordingly, it is possible, for example, to use frequencies in the range of 1 kHz (purely inductive coupling) to 1 GHz (electromagnetic coupling), and in particular in the range of 13 MHz (primarily inductive coupling).

In this way, another (in particular implantable) medical device (such as an ICD or a cardiac pacemaker) can experience an electrical excitation of the muscle cells by way of wireless communication, or poll this from the sensor, or measure this with the aid of the sensor.

According to one embodiment, the antenna structure comprises an electrical conductor, which has a first end and a second end, wherein each of the two ends is connected to the dielectric component.

According to one embodiment, the aforementioned electrical conductor furthermore has a loop-shaped design.

According to one embodiment, the antenna structure can furthermore comprise a further electrical conductor, which preferably likewise has a loop-shaped design, wherein the further electrical conductor has a first end and a second end, wherein the two ends of the further electrical conductor are, in turn, each connected to the dielectric component.

According to an alternative embodiment in terms of the antenna structure, it is provided that the sensor includes an inductor in the form of a coil structure, which is connected to the dielectric component. The coil structure can, for example, be formed by a coil that comprises an electrical conductor including multiple windings, wherein the electrical conductor has two ends, which are connected, in particular galvanically, to the dielectric component, for example by way of a welded joint, a soldered joint or an electrically conducting adhesive bond.

According to one embodiment, it can be provided in this regard that the coil structure and the dielectric component form a resonant circuit, so that a resonant frequency of the resonant circuit changes when the electric field in the dielectric component and the capacitance of the dielectric component change with an electrical excitation of the muscle cells.

The change in the resonant frequency can, in turn, be ascertained using known methods (by way of wireless communication), for example by way of an (in particular implantable) medical device (for example in the form of an ICD or a cardiac pacemaker).

According to one embodiment, it is furthermore provided that the coil structure comprises two spiral-shaped electrical conductors, wherein the two spiral-shaped electrical conductors are each connected to the dielectric component, wherein in particular the respective spiral-shaped electrical conductor is connected to the dielectric component via an end of the respective spiral-shaped conductor.

According to one embodiment, it is furthermore provided that the sensor comprises a fastening element for fastening the sensor to the tissue (in particular muscle tissue or cardiac muscle tissue) of a patient, wherein the fastening element is in particular fixed to the dielectric component.

According to one embodiment, the fastening element can have a screw-like design (for example in the form of a helical wire).

According to one embodiment, it is furthermore provided that the contact point is formed by the fastening element.

According to one embodiment, it is furthermore provided that the sensor includes a further contact point for electrically contacting muscle cells of a patient, which is connected to the dielectric component in an electrically conducting manner.

According to one embodiment of the sensor, it is furthermore provided that the dielectric component comprises a capacitor or is formed by a capacitor. The capacitor can be a class 2 or class 3 ceramic capacitor. As an alternative, the effect of the change in capacitance can be achieved by applying a voltage using a microelectromechanical system (MEMS) capacitor.

According to a further embodiment, it is provided that the dielectric component (or the capacitor) comprises a ferroelectric substance, and in particular barium titanate or lead zirconate titanate.

A further aspect relates to a system, comprising an implantable sensor disclosed herein, and an implantable medical device (in particular in the form of an implantable cardiac pacemaker or an implantable cardioverter defibrillator), wherein the medical device is preferably configured for wirelessly measuring or polling an excitation of muscle cells detected by the sensor.

In particular in the event that an antenna structure is used (see above), the implantable medical device can be designed to transmit a preferably broadband electromagnetic signal to the sensor, and to evaluate the reflection behavior of the antenna structure, which represents a measure of the activity of the electrical excitation of the muscle cells or cardiac muscle cells present at the site of the dielectric component. The broadband nature can, for example, be selected based on the change in capacitance, and thus the change in the resonant frequency, of the sensor. In this way, it is possible to use a bandwidth in the range of 10 kHz, for example. Depending on the frequency range used, it is advantageous when the bandwidth is at least 10% of the medium frequency. As an alternative, the resonant frequency can also take place by way of a frequency sweep for this frequency range.

In particular in the event that, as an alternative, an inductor in the form of a coil structure is used, which together with the dielectric component forms a resonant circuit (see above), the implantable medical device can be designed to measure the resonant frequency of the resonant circuit, which changes with an electrical excitation of muscle cells.

The system can comprise multiple sensors so as to, in particular, improve the measurement results. In the process, it is also possible to use several different sensors. The sensors can then, for example, be polled individually and/or collectively by the implantable medical device.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Exemplary embodiments will be described hereafter in detail based on the figures. In the drawings.

DETAILED DESCRIPTION OF THE INVENTION

The disclosure relates to an implantable sensor 1 for detecting an electrical excitation of muscle cells M, in particular cardiac muscle cells M of a heart H of a patient, as is shown in FIGS. 1 to 4, for example.

It is provided in the process that the sensor 1 comprises a dielectric component 2 and at least one contact point 20 for contacting the muscle cells M, which is connected to the dielectric component 2, so that an electric field in the dielectric component 2, and correspondingly a capacitance of the dielectric component 2, change with an electrical excitation of the muscle cells M.

Figure 1:
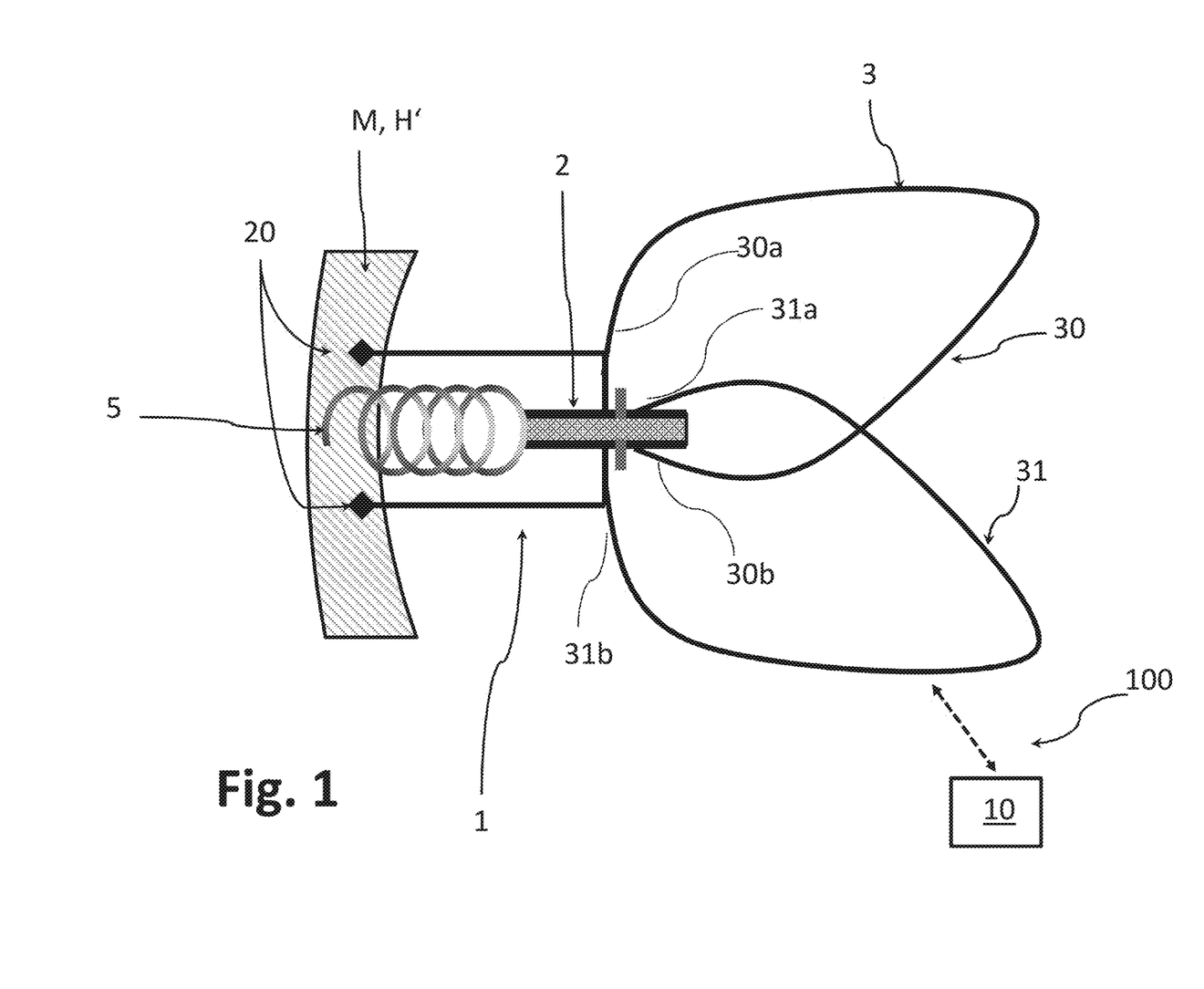
FIG. 1 shows a schematic illustration of an embodiment of a sensor comprising a dielectric component and an antenna structure.
Figure 2:
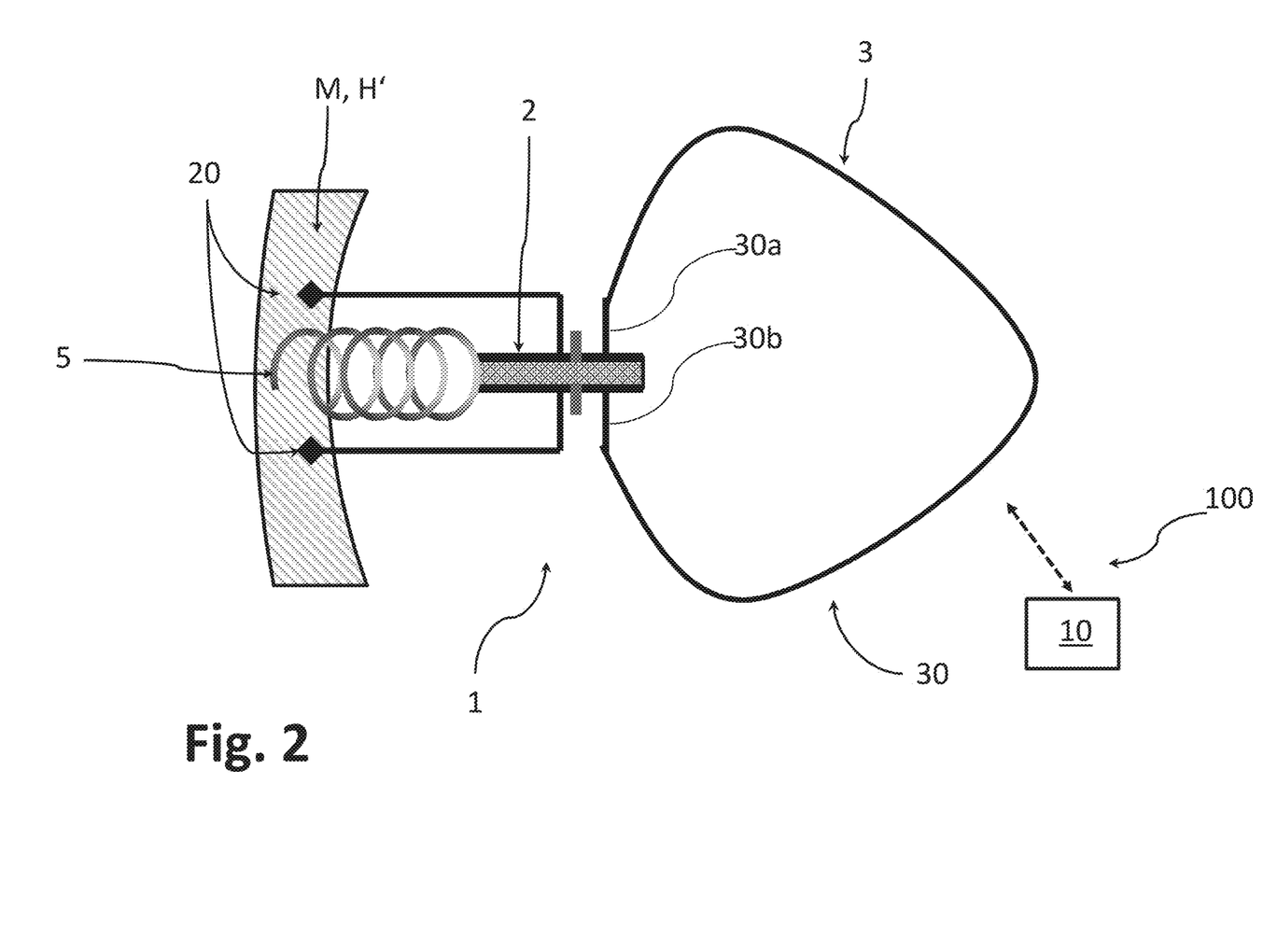
FIG. 2 shows a schematic illustration of another embodiment of a sensor comprising a dielectric component and an antenna structure.

According to a first variant, which is shown in FIGS. 1 and 2, for example, the sensor 1 comprises an implantable body including an antenna structure 3, a dielectric component 2 and, for example, two contact points 20 to the tissue M. The sensor 1 can comprise a fixed housing for accommodating the components of the sensor; however, this is not absolutely necessary. For example, a flexible plastic film can be used as carrier material (for example a flexible conductive track). Depending on the material of the dielectric (biocompatibility), an encapsulation of the capacitor may be provided.

By applying an electric field (stimulus transmission of the cardiac muscle cells), the capacitance of the dielectric component 2 is changed. As a result, the adaptation of the antenna structure 3 changes, which can be measured by way of a broadband electromagnetic signal, which is transmitted from an implantable medical device 10 (for example ICD or cardiac pacemaker) to the sensor 1.

According to FIG. 1, the antenna structure 3 can comprise two loop-shaped electrical conductors 30, 31, which are each connected via the ends 30a, 30b, or 31a, 31b thereof to the dielectric component 2.

The sensor 1 can furthermore be connected to the muscle tissue M by way of a fastening element 5, here, for example, in the form of a screw.

FIG. 2 shows a modification of the embodiment shown in FIG. 1, in which the antenna structure 3 is formed by a single loop-shaped electrical conductor 30, which is connected, via the ends 30a, 30b thereof, to the dielectric component 2.

A basic functional principle of a sensor 1 according to FIGS. 1 and 2 can be described as follows. If the change in relative permittivity is known, the change in the capacitance, and thus the detuning of the resonant frequency of the simple capacitor system according to FIG. 7 can be estimated. According to the publication Rehrig, P., et. al., "Dielectric and Electromechanical Properties of Barium Titanate Single Crystals Grown by Templated Grain Growth", IEEE Transactions on Ultrasonics, Ferroelectrics, and Frequency Control, Vol. 47, No. 4, July 2000, it is possible, for example, to use the relative permittivity as a function of the intensity of the electric field for a $BaTiO_3$ crystal to approximately calculate the relative permittivity around the zero point as $\varepsilon_r = 600 - 500 * 10^{-6} * U/d$.

Figure 7:
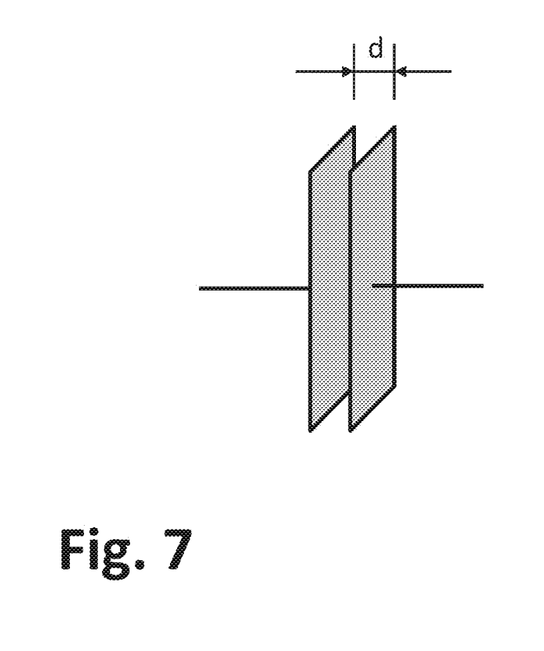
FIG. 7 shows a schematic illustration of a capacitor.

Using this estimation in the equation for calculating the plate capacitor $C = \varepsilon_0 * \varepsilon_r * A/d$ according to FIG. 7 yields a capacitance that is dependent on the voltage (where: C=capacitance of the system, $\varepsilon_0$=permittivity of the vacuum, A=surface of the capacitor plates, d=distance of the capacitor plates).

Figure 8:
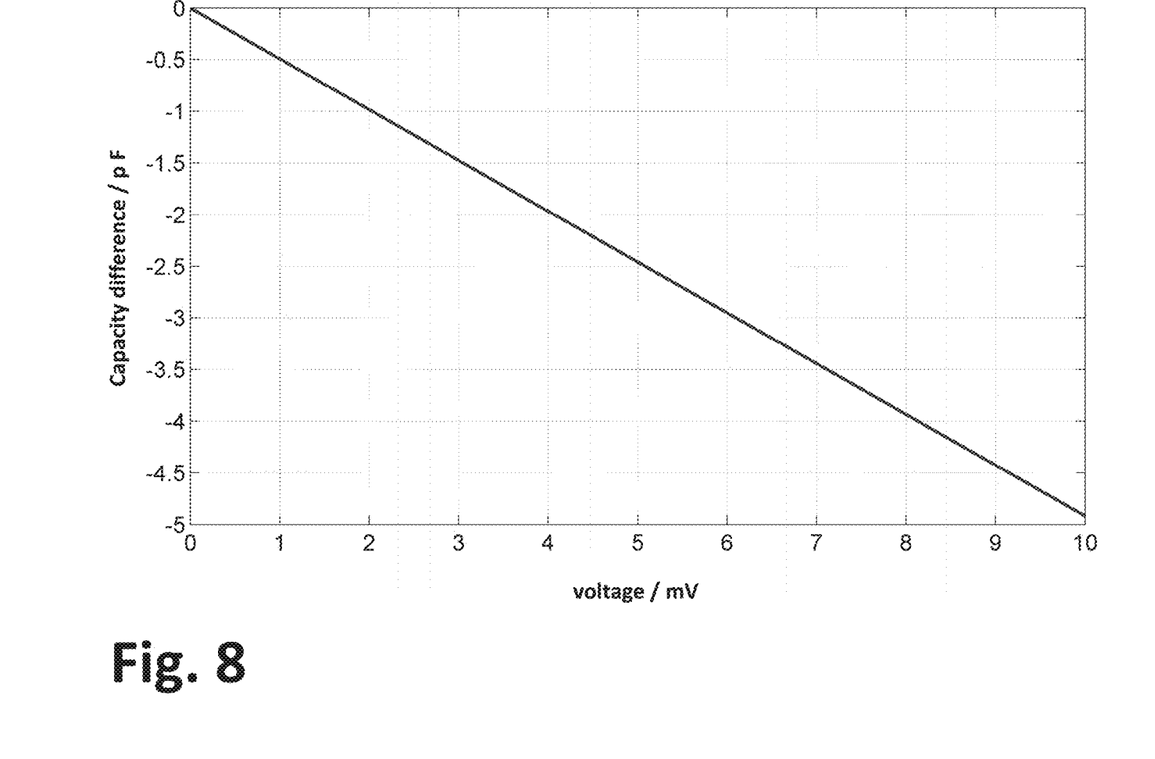
FIG. 8 shows an illustration of the change in capacitance as a function of a present voltage.

If, for example, numerical values are used (A=1000 µm*1000 µm, d=3 µm), a change in the capacitance corresponding to FIG. 8 is obtained.

Figure 9:
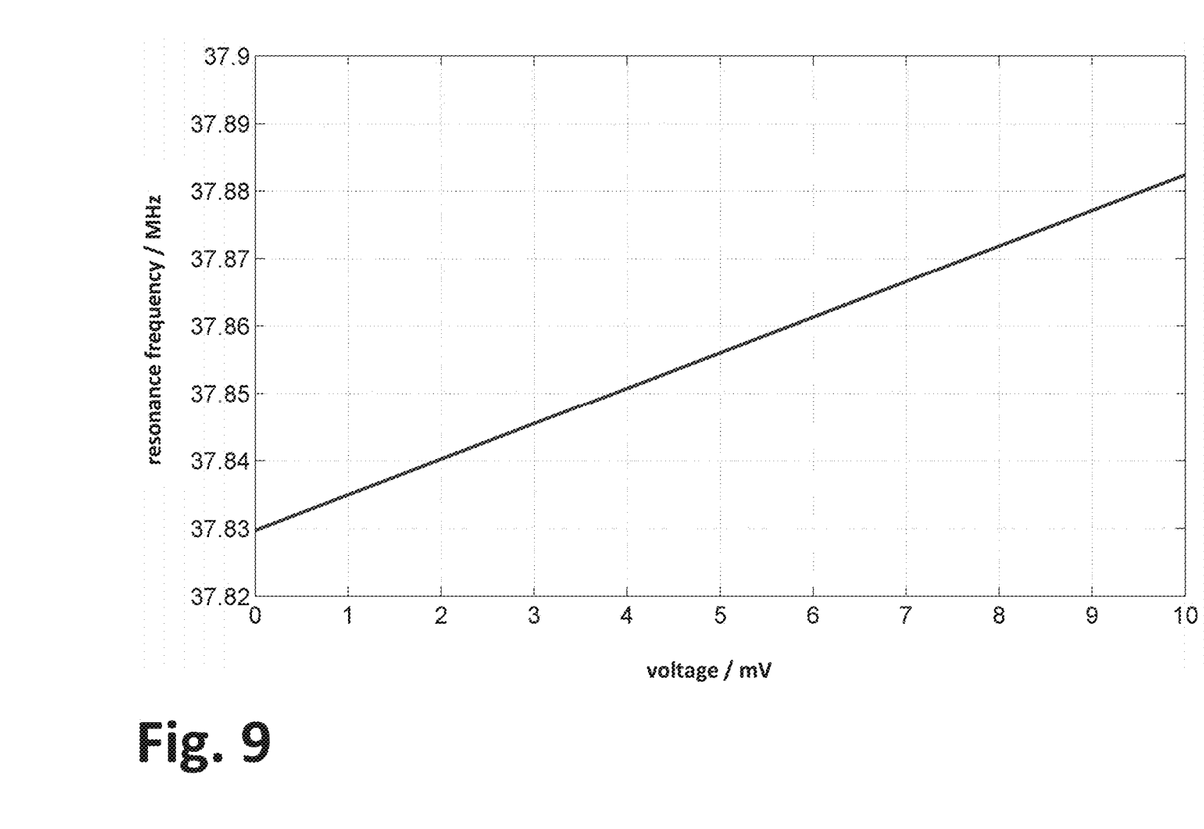
FIG. 9 shows an illustration of the change in resonant frequency as a function of the present voltage.

Using Thomson's oscillation equation $f_0 = 1/(2*\pi*\sqrt{L*C})$, it is possible to determine the resonant frequency of a resonant circuit with a voltage-dependent capacitance by inserting L and C. If the parameters according to FIG. 7 and FIG. 8 are selected, and L=10 nF is set, a change in the resonant frequency according to FIG. 9 is obtained, which can be measured in the known manner (for example by the implantable medical device 10).

The respective antenna structure 3 (for example according to FIGS. 1 and 2) can be formed by a metallically coated film, for example, wherein the metal is preferably gold or platinum, and is preferably matched by way of the series connected dielectric 2 in such a way that the combination of the antenna structure 3 and the capacitor 2 has electromagnetic resonance for a frequency band in the ultra-high frequency range, without an external static electric field.

In the case of an external applied electric field, the dielectric 2 preferably exhibits a strongly non-linear behavior and thus, depending on the field strength (stimulus transmission of the cardiac muscle cells M), detunes the resonant behavior of the antenna structure 3. For example, class 2 ceramic capacitors 2, and in particular the class 2 ceramic types Y5V and Z5U (according to EIA RS-198 or according to IEC 60384-9/IEC 60384-22:2E6 and 2F4), are suitable for this purpose. These ceramics share the common trait that they are produced based on ferroelectric substances such as barium titanate or lead zirconate titanate. Barium titanate is preferred for implants due to the biocompatibility thereof.

Electrical signals, which arise due to stimulus transmission during activity of the cardiac muscle cells, form weak electric fields, which directly impact the resonance behavior of the antenna structure 3. If the antenna structure 3 is excited by way of a transmitter having the frequency f0 in the UHF range, for example using a broadband impulse having the bandwidth Δf, where Δf is in the range of 10 kHz to 1 MHz, the reflection behavior of the antenna structure 3 provides a measure of the activity of the cardiac heart muscles M present at the site of the dielectric 2.

Figure 3:
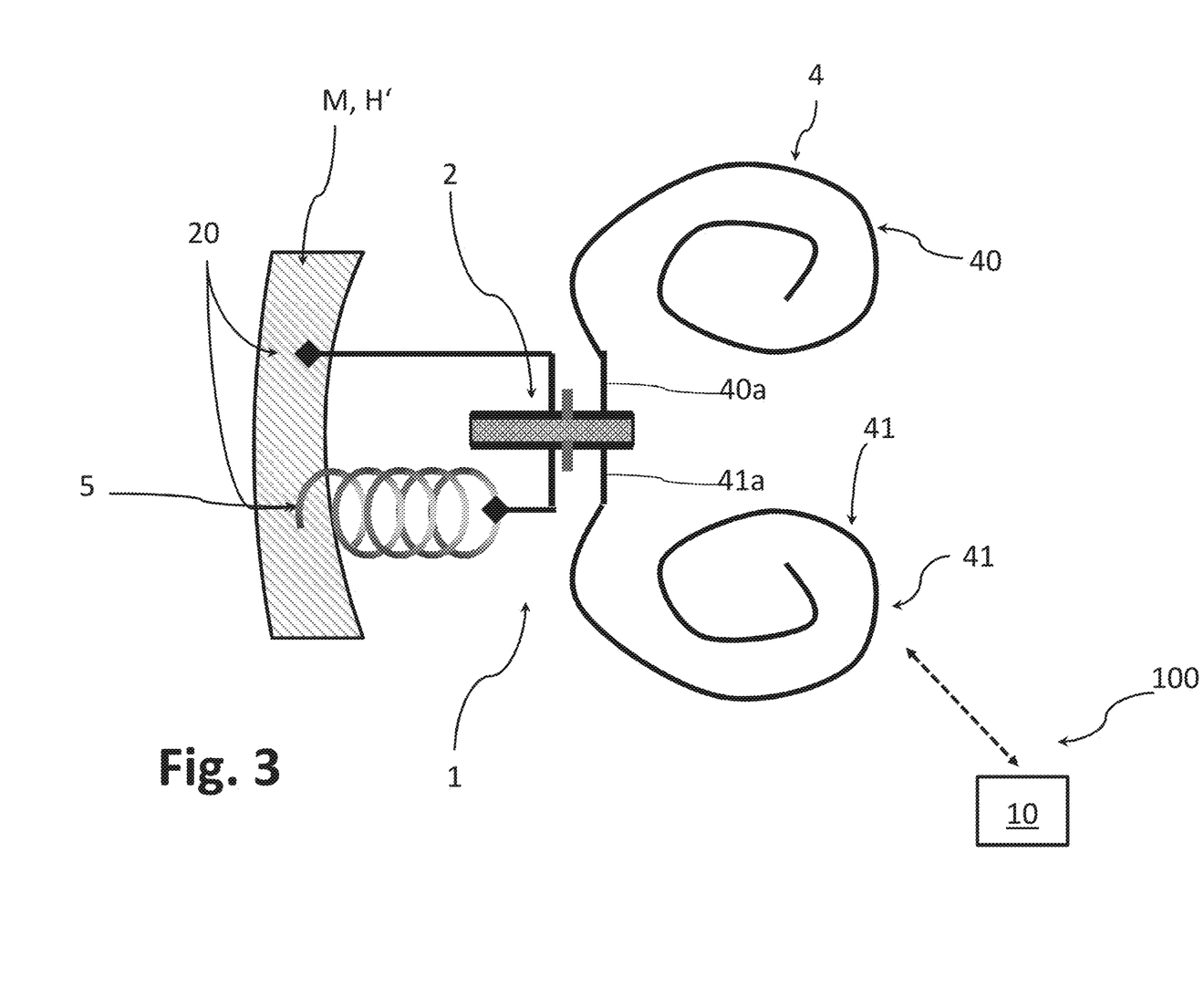
FIG. 3 shows a schematic illustration of another embodiment of a sensor comprising a dielectric component and a coil structure.
Figure 4:
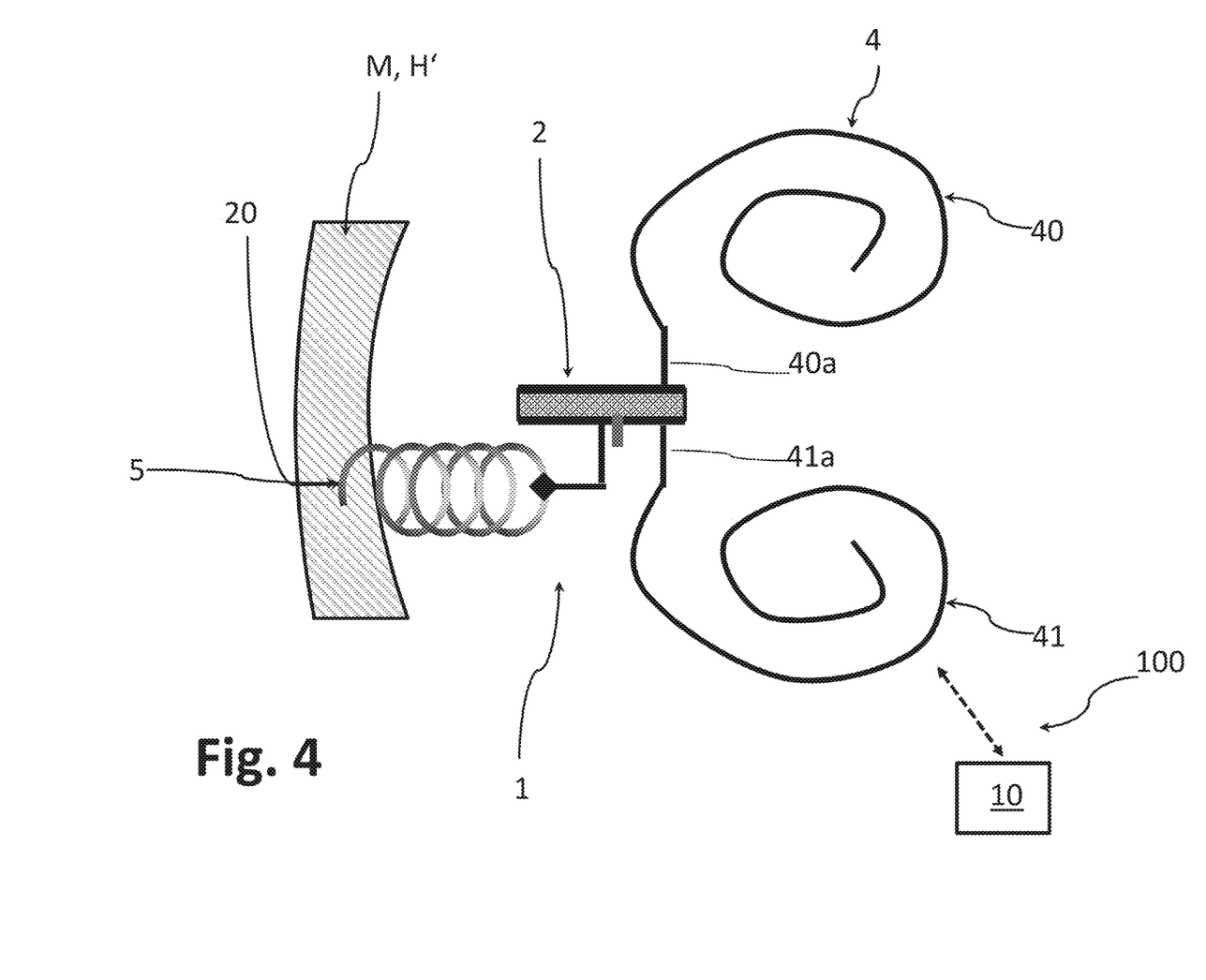
FIG. 4 shows a schematic illustration of another embodiment of a sensor comprising a dielectric component and a coil structure.

FIGS. 3 and 4 each show an alternative (second) variant of a sensor 1. According to FIG. 3, it is provided, for example, that the sensor 1 comprises an implantable body including a coil structure 4, a dielectric component 2, and at least one contact point 20 to the tissue or the muscle cells (here, in particular, cardiac muscle cells) M.

In the case of an external applied electric field, the dielectric 2 preferably again exhibits a strongly non-linear behavior and thus, depending on the field strength, detunes the resonant frequency of the resonant circuit 2, 4 since the capacitance of the dielectric component 2 changes. The change in the resonant frequency of the resonant circuit made up of the coil structure 4 and the dielectric component 2 can be measured by way of near field coupling by a magnetic field using an implantable medical device 10. The resonant circuit 2, 4 is in particular preferably resonant in a frequency range in which purely magnetic coupling can be assumed.

The resonant frequency is furthermore preferably selected to be as high as possible, so as to obtain a small form factor and high sensitivity with the change in capacitance. The frequency is upwardly limited by the adherence to the magnetic coupling.

The resonant frequency can be determined by the implantable medical device 10, in particular using methods known from the literature, and thus supplies a measure of the activity of the cardiac muscle cells present at the site of the dielectric 2.

According to FIG. 3, for example, the sensor 1 can be fixed to the muscle tissue M by way of a fastening element 5 (for example in the form of a screw), which also acts as the contact point 20. The sensor 1, or the dielectric component 2, can be connected to the muscle cells M by way of a further contact point 20.

As an alternative, the sensor 2 can only be connected by way of the fastening element 5, which also represents the contact point 20, to the muscle cells or cardiac muscle cells M.

The coil structure 4 of the embodiments shown in FIGS. 3 and 4 can, for example, be formed by two spiral-shaped electrical conductors 40, 41, wherein each of the two spiral-shaped electrical conductors 40, 41 is connected by an end 40a, 41a to the dielectric component 2.

Here as well, the dielectric component 2 of the sensors according to FIGS. 3 and 4 is preferably based on a ferroelectric ceramic material (see above) and can, for example, be a class 2 ceramic capacitor, which can be designed as described above. In all embodiments, the capacitor 2 can be composed of multiple ceramic layers (so-called multilayer ceramic capacitor, MLCC).

The sensor 1, as it is shown in FIGS. 1 to 4 in individual embodiments, for example, is furthermore preferably configured and provided to be arranged in the atrium A or to be implanted in the coronary sinus of the heart H (the HIS bundle in the ventricle is also a potential position), wherein the at least one contact point 20 (or the two contact points 20) preferably makes contact with muscle cells or cardiac muscle cells M. The sensor 1 is furthermore preferably anchored in the cardiac wall H' by way of the fastening element 5.

Furthermore, a sensor 1 (see FIGS. 1 to 4, for example), together with an implantable medical device 10, can form a system 100, wherein the device 100 (for example ICD or cardiac pacemaker) is designed to measure the change in the adaptation of the antenna structure 3 (FIGS. 1 and 2) or the change in the resonant frequency of the resonant circuit 2, 4 (FIGS. 3 and 4), so as to wirelessly detect the electrical excitation of the muscle cells M.

Figure 5A:
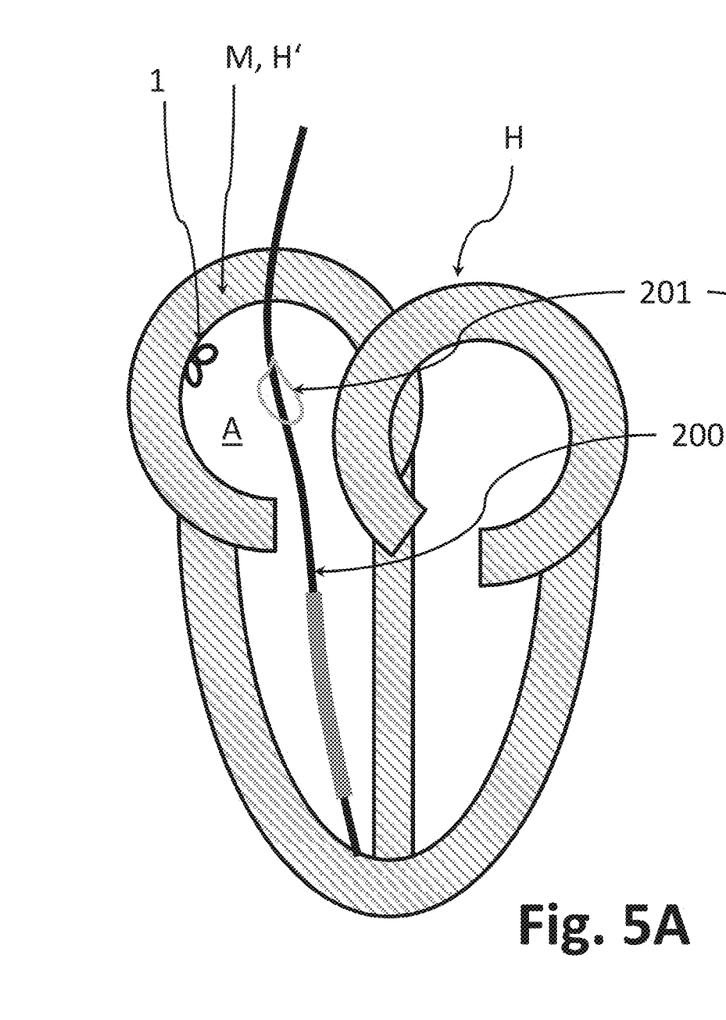
FIGS. 5A-B show an implanted sensor, which is anchored in the cardiac wall, and an electrode lead including an antenna for polling the electrical excitation of the muscle cells contacted by way of the sensor, wherein the polling antenna can be positioned inside the heart (A) or outside the heart (B)
Figure 5B:
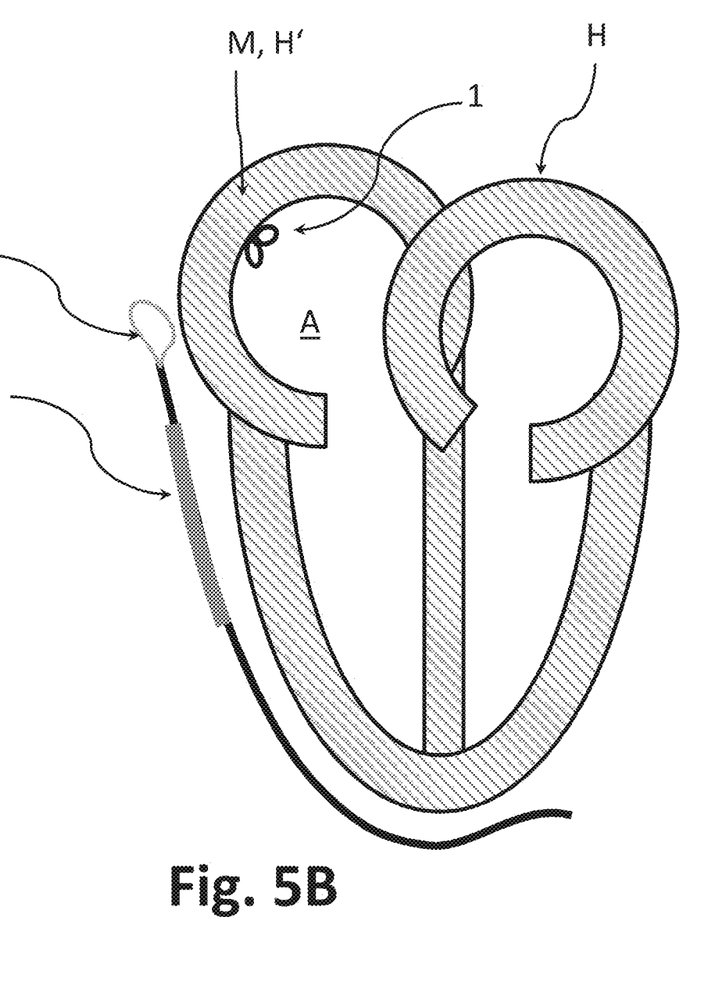

The approach disclosed here, in particular, advantageously dispenses both with a hard-wired connection to the sensor and with a battery in the sensor 1 itself. The activity of the cardiac muscle cells M is in particular wirelessly transmitted between an implantable medical device 10 and the sensor 1. This minimizes the costs and complexity of the sensor 1. By dispensing with an additional hard-wired connection to the sensor, the system 100 is robust, and enables new approaches in treatment, for example in the case of extra-cardiac bradycardia/tachycardia treatment (see FIG. 5B). In FIGS. 5A and 5B, the electrode lead 200 forms both a carrier of the antenna 201 for polling the signals of the sensor 1, and an electrical connection to the active implant.

Figure 6:
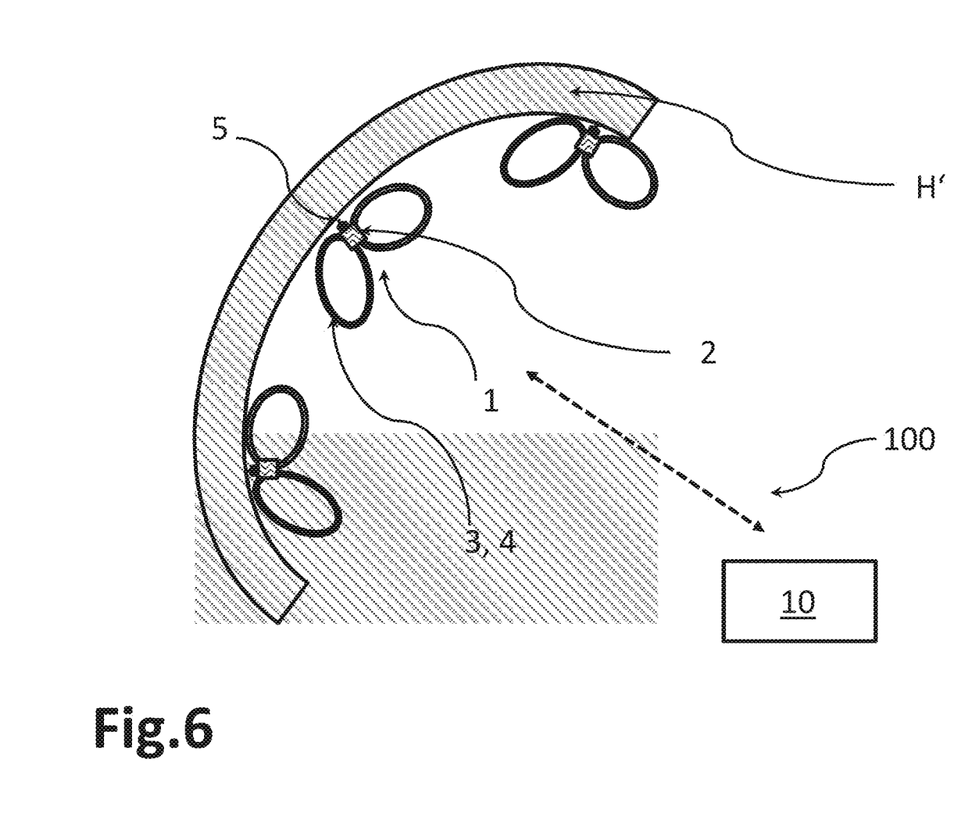
FIG. 6 shows the option of using multiple sensors for detecting electrical excitations of muscle cells or cardiac muscle cells.

In addition to permanently measuring the electrical excitation of the muscle cells M, it is also conceivable to sequentially poll the measurement data (for example, if needed, in addition to conventional measurement or for synchronization purposes). The small form factor additionally makes it possible to implant multiple of the wireless sensors 1 in different positions in the cardiac wall H', as is shown in FIG. 6, for example. The individual sensors 1 can, in particular, have different resonant frequencies and can be addressed deliberately or collectively by suitable pulses.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

The invention claimed is:

1. An implantable sensor for detecting an electrical excitation of muscle cells, including cardiac muscle cells, wherein the sensor comprises a dielectric component and a contact point for contacting muscle cells, which is connected to the dielectric component, so that an electric field in the dielectric component and, correspondingly, a capacitance of the dielectric component change with an electrical excitation of the muscle cells.

2. The implantable sensor according to claim 1, wherein the sensor is a passive sensor.

3. The implantable sensor according to claim 1, wherein the sensor is designed to wirelessly transmit the detection of an excitation of the muscle cells to a medical device, the medical device comprising an implantable medical device.

4. The implantable sensor according to claim 1, wherein the sensor includes an antenna structure, which is connected to the dielectric component.

5. The implantable sensor according to claim 4, wherein the antenna structure is connected to the dielectric component so that the adaptation of the antenna structure changes when the electric field in the dielectric component and the capacitance of the dielectric component change with an electrical excitation of the muscle cells.

6. The implantable sensor according to claim 4, wherein the antenna structure comprises an electrical conductor, which has a first end and a second end, each of the first and second ends being connected to the dielectric component.

7. The implantable sensor according to claim 6, wherein the electrical conductor has a loop-shaped design.

8. The implantable sensor according to claim 6, wherein the antenna structure comprises a further electrical conductor, which has a loop-shaped design, the further electrical conductor having a first end and a second end, each of the first and second ends of the further electrical conductor being connected to the dielectric component.

9. The implantable sensor according to claim 1, wherein the sensor includes an inductor in the form of a coil structure, which is connected to the dielectric component.

10. The implantable sensor according to claim 9, wherein the coil structure and the dielectric component form a resonant circuit, so that a resonant frequency of the resonant circuit changes when the electric field in the dielectric component and the capacitance of the dielectric component change with an electrical excitation of the muscle cells.

11. The implantable sensor according to claim 9, wherein the coil structure comprises two spiral-shaped electrical conductors the two spiral-shaped electrical conductors each being connected to the dielectric component, wherein the respective spiral-shaped electrical conductor being connected to the dielectric component via an end of the respective spiral-shaped conductor.

12. The implantable sensor according to claim 1, wherein the sensor comprises a fastening element for fastening the sensor to the tissue of a patient, the fastening element being fixed to the dielectric component.

13. The implantable sensor according to claim 12, wherein the contact point is formed by the fastening element.

14. The implantable sensor according to claim 1, wherein the sensor includes a further contact point for contacting muscle cells, which is connected to the dielectric component.

15. A system, comprising at least one implantable sensor according to claim 1, and an implantable medical device, wherein the medical device is configured to measure an excitation of muscle cells detected by the at least one sensor.

* * * * *